Figure 1:
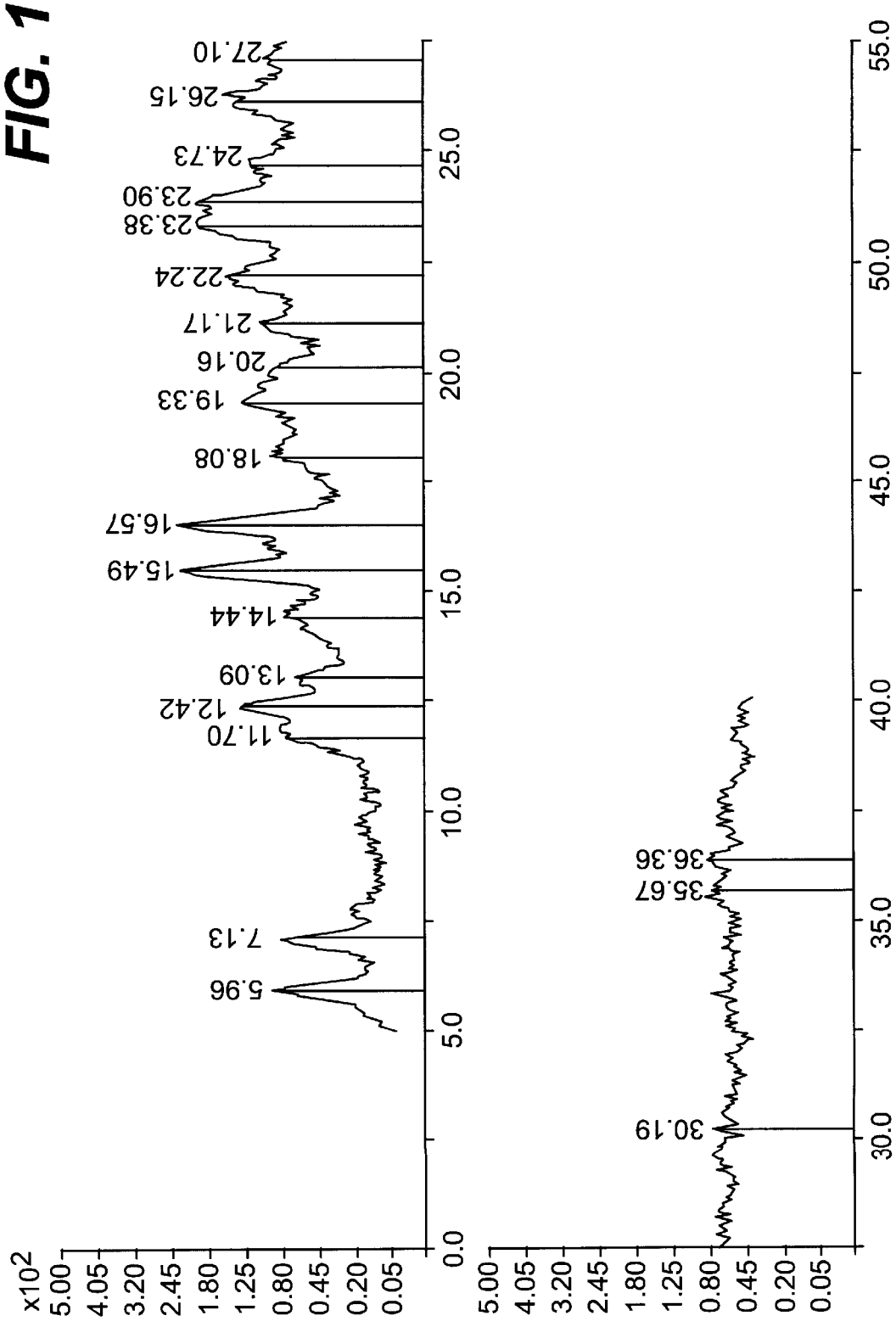

United States Patent [19]
Didier et al.

[11] Patent Number: 6,150,541
[45] Date of Patent: Nov. 21, 2000

[54] 4,10-β-DIACETOXY-2α-BENZOYLOXY-5β,20-EPOXY-1-HYDROXY-9-OXO-19-NORCYCLOPROPA[G]TAX-11-EN-13α-YL (2R,3S)-3-TERT-BUTOXYCARBONYLAMINO-2-HYDROXY-3-PHENYLPROPIONATE DIHYDRATE AND ITS PROCESS OF PREPARATION

[75] Inventors: Eric Didier, Paris; Michel Lavigne, Chilly-Mazarin; Jean-René Authelin, Saint-German-les-Arpajon, all of France

[73] Assignee: Aventis Pharma S.A., Antony, France

[21] Appl. No.: 09/367,387

[22] Filed: Jun. 10, 1998

Related U.S. Application Data

[63] Continuation-in-part of application No. PCT/FR96/01957, Dec. 9, 1996.

[30] Foreign Application Priority Data

Dec. 14, 1995 [FR] France ..................................... 95 14841

[51] Int. Cl.$^7$ .................................................. C07D 305/14
[52] U.S. Cl. ............................................. 549/510; 549/511
[58] Field of Search ...................................... 549/510, 511

[56] References Cited

U.S. PATENT DOCUMENTS 5,723,635  3/1998  Durand et al. ........................ 549/510

OTHER PUBLICATIONS

Chemical Abstracts, vol. 113, No. 75, 1990.
ACTA Crystallograph. Sect. C: Crystal Structure Commun., vol. C46, No. 5, 190, pp. 781–784, 1990.

*Primary Examiner*—Ba K. Trinh
*Attorney, Agent, or Firm*—Finnegan, Henderson, Farabow, Garrett, & Dunner, L.L.P.

[57] ABSTRACT

The present invention is directed to 4,10β-diacetoxy-2α-benzoyloxy-5β,20-epoxy-1-hydroxy-9-oxo-19-norcyclopropa(g)tax-11-en-13α-yl (2r,3s)-3-tert-butoxycarbonylamino-2-hydroxy-3-phenylpropionate dihydrate and a process for its preparation.

6 Claims, 5 Drawing Sheets

4,10-β-DIACETOXY-2α-BENZOYLOXY-5β,20-EPOXY-1-HYDROXY-9-OXO-19-NORCYCLOPROPA[G]TAX-11-EN-13α-YL (2R,3S)-3-TERT-BUTOXYCARBONYLAMINO-2-HYDROXY-3-PHENYLPROPIONATE DIHYDRATE AND ITS PROCESS OF PREPARATION

This application is a continuation-in-part of PCT/FR96/01957, filed Dec. 9, 1996, which claims priority based on French application No. 95-14841 filed Dec. 14, 1995.

The present invention relates to 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate and to its preparation.

4,10β-Diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate exhibits notable anticancer and antileukaemic properties.

4,10β-Diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate is prepared according to the process which is described more particularly in International Application PCT WO 94/13654.

It has been found that 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate exhibits a stability which is markedly superior to that of the anhydrous product.

According to the invention, 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate can be obtained by crystallization of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate or by recrystallization of the dihydrate from a mixture of water and an aliphatic alcohol containing 1 to 3 carbon atoms or from a mixture of water and a ketone containing 3 to 4 carbon atoms, followed by drying the isolated product under reduced pressure and by optionally maintaining in a relative humidity greater than or equal to 40% or by direct drying in an atmosphere with a relative humidity greater than or equal to 40%.

In order to carry out the process according to the invention, it may be particularly advantageous—to dissolve 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate or its hydrate in an aliphatic alcohol containing 1 to 3 carbon atoms or in a ketone containing 3 to 4 carbon atoms, to treat the solution with water, to seed the solution with the dihydrate and then to treat again with water, to separate the crystals obtained, then to dry them under reduced pressure and then optionally to maintain them in an atmosphere with a relative humidity greater than or equal to 40%, that is to say, by way of example for a relative humidity of 40%, drying under a residual pressure of approximately 1.33 kPa for a temperature of 25° C. and under a residual pressure of approximately 3.86 kPa for a temperature of 45° C., or to dry them directly in an atmosphere with a relative humidity greater than or equal to 40%, that is to say, by way of example for a relative humidity of 40%, drying under a residual pressure of approximately 1.33 kPa for a temperature of 25° C. and under a residual pressure of approximately 3.86 kPa for a temperature of 45° C.

Generally, 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate or its hydrate is dissolved in an excess of aliphatic alcohol, preferably ethanol, or in an excess of a ketone, preferably acetone. Preferably, the amount of alcohol or ketone is between 4 and 16 parts by volume with respect to the weight of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate used.

Generally, the water is added such that the water/alcohol or water/ketone final volume ratio is between 1/3 and 3/1.

The 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate which crystallizes is separated, preferably by filtration or centrifuging. The drying or the optional maintaining in an atmosphere with a relative humidity greater than or equal to 40% is carried out under reduced pressure, generally of between 0.5 and 30 kPa, preferably in the region of 5 kPa, at a temperature of between 10 and 70° C., preferably in the region of 40° C.

The water activity isotherm of the product was studied. Thus, 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate samples, intentionally dehydrated by forced drying, were maintained in atmospheres of controlled relative humidity (HR) at 25° C. The water contents, determined by TGA, show that the products stabilize at contents in the region of 4% (between 3 and 5%) when the relative humidity is greater than or equal to 40% (theoretical water content of 4.15% for a dihydrate).

Water activity isotherm at 25° C.

| Initial drying conditions | Initial form by XD | Initial TGA | RH % | Residence time | Loss by TGA | Form by XD |
| --- | --- | --- | --- | --- | --- | --- |
| 20° C., 48 hours | Dihydrate | 1.6%/32 to 71° C. | 0 | 18 days | 0.8%/34 to 170° C. | Dihydrate |
|  |  |  |  | 31 days | 0.99%/33 to 55° C. | Dihydrate |

-continued

Water activity isotherm at 25° C.

| Initial drying conditions | Initial form by XD | Initial TGA | RH % | Residence time | Loss by TGA | Form by XD |
|---|---|---|---|---|---|---|
| 1.3 kPa | | Stability at weight from 71 to 200° C. | 5 | 55 days | 1.69%/32 to 63° C. | Dihydrate |
| | | | 11 | 55 days | 1.17%/33 to 65° C. | Dihydrate |
| | | | 20 | 19 days | 1.96%/33 to 68° C. | Dihydrate |
| | | | | 31 days | 2.06%/34 to 61° C. | Dihydrate |
| | | | 42 | 19 days | 3.77%/33 to 65° C. | Dihydrate |
| | | | | 31 days | 4.07%/34 to 60° C. | Dihydrate |
| | | | 58 | 19 days | 3.30%/34 to 63° C. | Dihydrate |
| | | | | 31 days | 3.59%/34 to 65° C. | Dihydrate |
| | | | 80 | 19 days | 3.98%/34 to 63° C. | Dihydrate |
| | | | | 31 days | 4.22%/34 to 65° C. | Dihydrate |
| | | | 98 | 19 days | 4.61%/34 to 68° C. | Dihydrate |
| | | | | 31 days | 4.63%/34 to 65° C. | Dihydrate |
| 60° C., 60 hours 4.6 kPa | Dihydrate | 0.76%/32 to 170° C. | 0 | 35 days | 0.85%/31 to 60° C. | Dihydrate |
| | | | 11 | 37 days | 0.90%/31 to 60° C. | Dihydrate |
| | | | 20 | 35 days | 0.95%/32 to 54° C. | Dihydrate |
| | | | 42 | 35 days | 3.51%/32 to 60° C. | Dihydrate |
| | | | 58 | 35 days | 2.35%/32 to 60° C. | Dihydrate |
| | | | 80 | 35 days | 3.75%/32 to 70° C. | Dihydrate |
| | | | 98 | 37 days | 3.97%/32 to 60° C. | Dihydrate |

In order to use the process according to the invention, it is possible to work directly on the ethanolic solution of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate obtained after deprotection in acid medium of 4,10β-diacetoxy-2α-benzoyloxy-5β,20-epoxy-1-hydroxy-9-oxo-19-norcyclopropa[g]tax-11-en-13α-yl (2R,4S,5R)-3-tert-butoxycarbonyl-2-(4-methoxyphenyl)-4-phenyloxazolidine-5-carboxylate.

The following examples illustrate the present invention.

EXAMPLE 1

Figure 5:
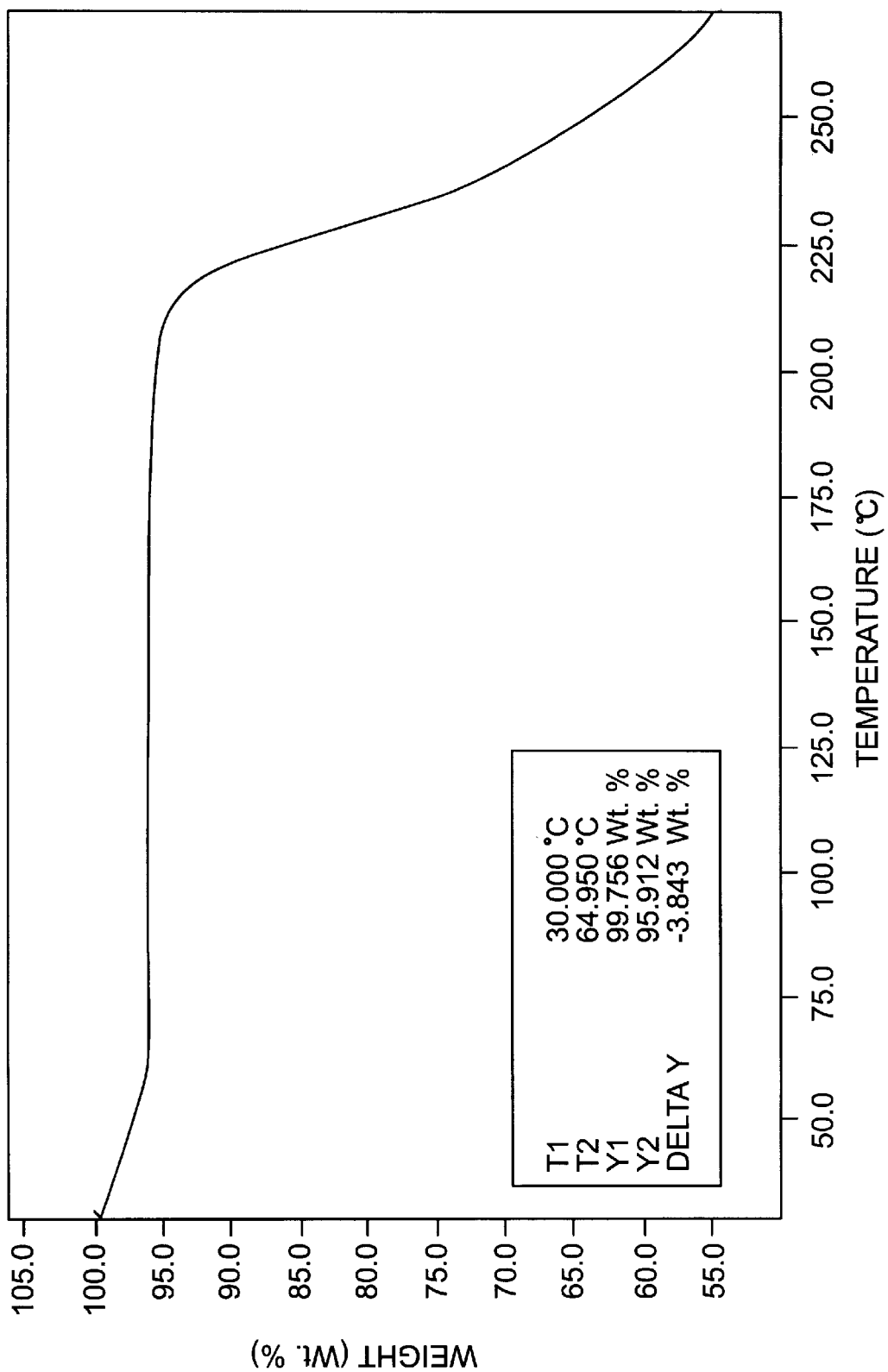

2 g of crude 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate and 20 cm³ of absolute ethanol were introduced into a three-necked flask. 20 cm³ of water were added over approximately 45 minutes to the stirred solution at 50° C. and the suspension obtained was then cooled to a temperature in the region of 20° C. After filtration, the product was washed on the filter with 20 cm³ of an absolute ethanol/water (1/1 by volume) mixture and the product was then dried at 40° C. under reduced pressure (5.3 kPa). 1.64 g of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate, containing 3.8% by TGA (FIG. 5) of water (theoretical value of the water content of the dihydrate of 4.15%), are obtained. The yield obtained was approximately 80%. The XRPD (X-ray powder diagram) diagram represented by FIG. 1 showed that the product thus obtained exhibited the characteristics of the dihydrate.

The X-ray powder diagram was obtained using a Philips PW 1700® device with a cobalt anti-cathode tube ($\lambda K_{\alpha 1}$=1.7889 Å), the sweeping was performed at an initial sweep angle of 5° 2–Θ, final sweep angle of 40° 2–Θ, with an increment of 0.02° 2–Θ, at a rate of 1 second per increment and using a silicon pastille.

Thermogravimetric analysis (TGA) was carried out using a Perkin-Elmer TGA 7® thermobalance at the initial temperature of 25° C. and at the final temperature of 300° C. with a temperature gradient of 10° C. per minute.

EXAMPLE 2

Figure 2:
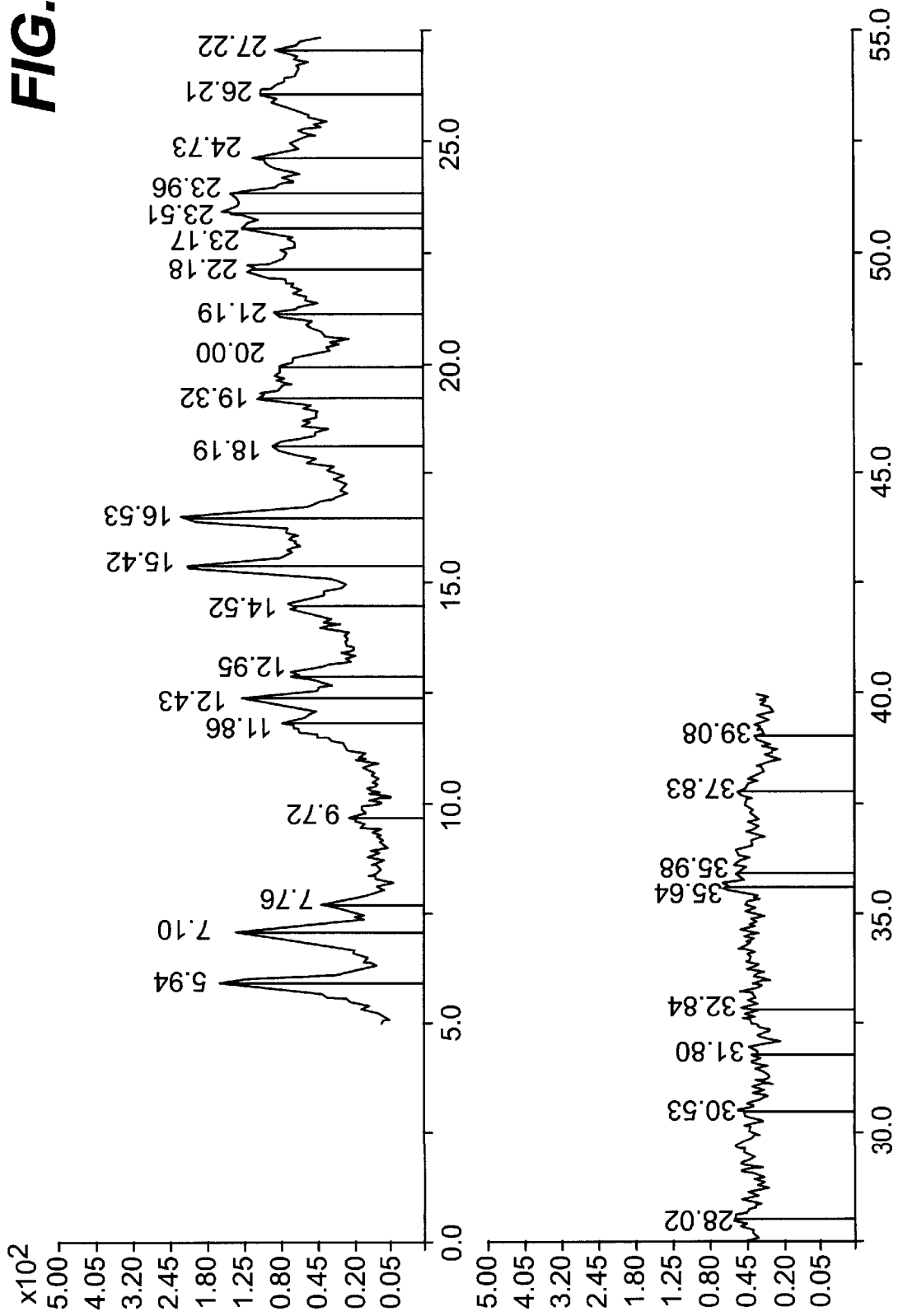

515 g of crude 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate and 4 litres of absolute ethanol were introduced into a reactor purged with nitrogen. The suspension was heated at 35–40° C. until dissolution is complete and the reactor was placed under reduced pressure of 8 kPa. Approximately 8 litres of solvent were distilled off at constant volume, the reactor was continuously supplied with ethanol (8 litres). After returning the reactor to atmospheric pressure, the solution was clarified by passing through a filter equipped with a 0.45 μm filter cloth. After rinsing the filter with 1 litre of absolute ethanol, approximately 1.8 litres of water were added at 40° C. over 1 hour to the whole of the solution. After initiating with 8 g of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate, the mixture was cooled at a temperature in the region of 20° C. for 15 hours. The suspension was then heated to 40° C. and then 1.66 litres of water were added over 4 hours. The mixture was cooled to a temperature in the region of 20° C. and left stirring for 17 hours. The suspension was filtered on sintered glass and the filtered product was washed with 1.25 litres of an alcohol/water (50/50 by volume) mixture. The product was dried in an oven at 35° C. at 5.3 kPa for 72 hours in the presence of a stock of water and then at 35° C. at 2.7 kPa for 8 hours without a stock of water and again at 35° C. at 5.3 kPa for 16 hours in the presence of a stock of water. 491 g of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate containing 4.0% of water (earl Fischer) were thus obtained. The XRPD (X-ray powder diagram) diagram represented by FIG. 2 showed that the product thus obtained was in the form of a dihydrate (theoretical value of the water content of 4,10β-diacetoxy-2α-benzoyloxy-5β,20-epoxy-1- hydroxy-9-oxo-19-norcyclopropa[g]tax-11-en-13α-yl (2R,3S)-3-tert-butoxycarbonylamino-2-hydroxy-3-phenylpropionate dihydrate of 4.15%).

The X-ray powder diagram was obtained under the conditions described in Example 1.

EXAMPLE 3

Figure 3:
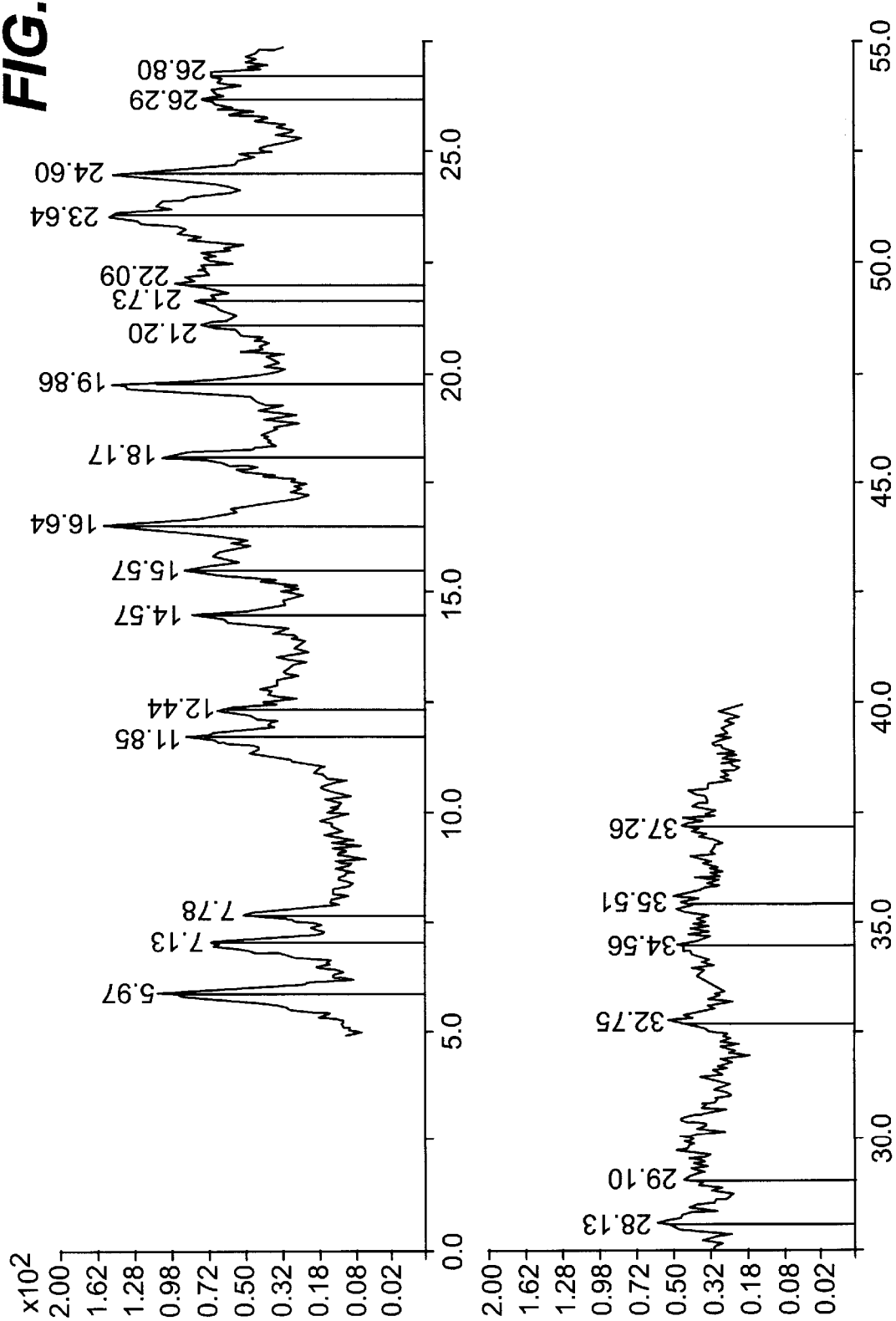

2 g of crude 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate and 20 cm³ of acetone were introduced into a three-necked round-bottomed flask. The solution obtained, which was stirred at a temperature in the region of 20° C., was treated with 20 cm³ of water over approximately 35 minutes. The suspension obtained was stirred for approximately 15 minutes. After filtration, the product was washed twice on the filter with 20 cm³ of an acetone/water (1/1 by volume) mixture and the product was then dried at 40° C. under reduced pressure (5.3 kPa). 1.28 g of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate were thus obtained. The yield obtained was approximately 75%. The XRPD (X-ray powder diagram) diagram represented by FIG. 3 showed that the product thus obtained exhibited the characteristics of the dihydrate.

The X-ray powder diagram was obtained under the conditions described in Example 1.

EXAMPLE 4

Figure 4:
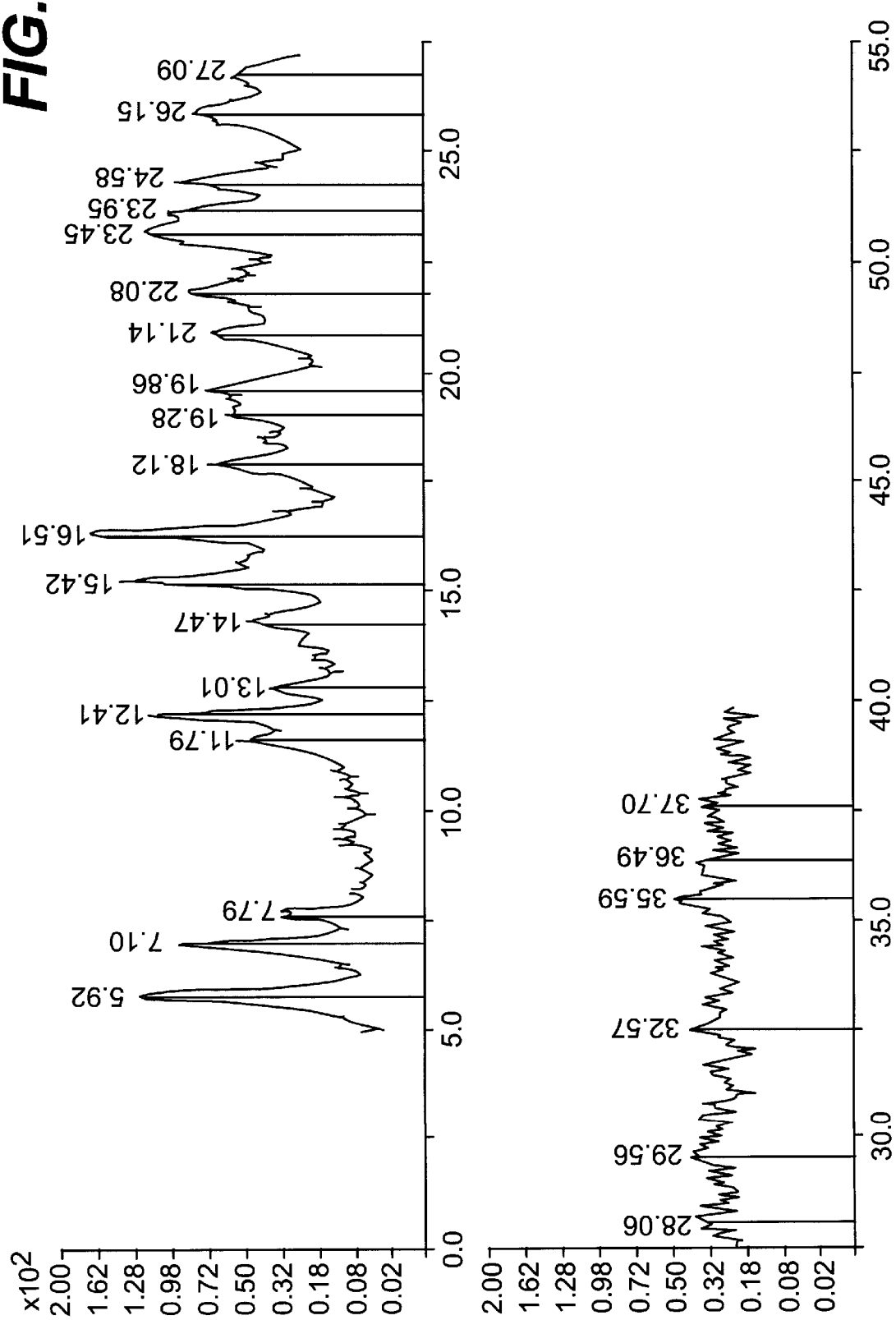

120 g of 4,10β-diacetoxy-2α-benzoyloxy-5β,20-epoxy-1-hydroxy-9-oxo-19-norcyclopropa[g]tax-11-en-13α-yl (2R,4S,5R)-3-tert-butoxycarbonyl-2-(4-methoxyphenyl)-4-phenyloxazolidine-5-carboxylate and 1.08 litres of ethyl acetate were introduced into a reactor purged with nitrogen. The suspension was stirred at a temperature in the region of 20° C. and then a solution of 3.25 cm³ of 36% hydrochloric acid in 17.6 cm³ of water was introduced. After maintaining for 3 hours 30 minutes, a solution of 3.5 g of sodium hydrogencarbonate in 350 cm³ of water was charged to the reactor and stirring was carried out for 15 minutes. After separation by settling and drawing off the aqueous phase, washing was carried out twice in succession with 350 cm³ of water. The organic phase was concentrated under reduced pressure at approximately 25° C. until a residual volume of 350 cm³ was reached and then 350 cm³ of absolute ethanol were introduced. Distillation under reduced pressure was resumed at approximately 30° C. until the ethyl acetate was exhaustively removed, while supplying with 1.5 litres of absolute ethanol. The solution was heated to 40° C. and then 470 cm³ of water were added over 15 minutes. The solution was seeded with a suspension of 1 g of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate in a mixture of 40 cm³ of water and 40 cm³ of absolute ethanol. After maintaining for 15 hours at approximately 40° C., 410 cm³ of water were added over 4–5 hours and the suspension was then cooled to 20° C. After filtration and washing the product on the filter, the product was dried for 15 hours under reduced pressure (2.7 kPa) at 25° C. and then for 24 hours at 35° C. 102 g of 4,10β-diacetoxy-2α-benzoyloxy-5β,20-epoxy-1-hydroxy-9-oxo-19-norcyclopropa[g]tax-11-en-13α-yl (2R,3S)-3-tert-butoxycarbonylamino-2-hydroxy-3-phenylpropionate dihydrate, containing 4.3% of water (Karl Fischer), were thus obtained with a yield of approximately 93%. The XRPD (X-ray powder diagram) diagram represented by FIG. 4 showed that the product thus obtained exhibited the characteristics of the dihydrate.

The X-ray powder diagram was obtained under the conditions described in Example 1.

What is claimed is:

1. 4,10β-diacetoxy-2α-benzoyloxy-5β,20-epoxy-1-hydroxy-9-oxo-19-norcyclopropa(g)tax-11-en-13α-yl (2R,3S)-3-tert-butoxycarbonylamino-2-hydroxy-3-phenylpropionate dihydrate.

2. A process for the preparation of 4,10β-diacetoxy-2α-benzoyloxy-5β,20-epoxy-1-hydroxy-9-oxo-19-norcyclopropa(g)tax-11-en-13α-yl (2R,3S)-3-tert-butoxycarbonylamino-2-hydroxy-3-phenylpropionate dihydrate;

wherein 4,10β-diacetoxy-2α-benzoyloxy-5β,20-epoxy-1-hydroxy-9-oxo-19-norcyclopropa(g)tax-11-en-13α-yl (2R,3S)-3-tert-butoxycarbonylamino-2-hydroxy-3-phenylpropionate or its hydrate is crystallized from a mixture of water and an aliphatic alcohol containing 1 to 3 carbon atoms or from a mixture of water and a ketone containing 3 to 4 carbon atoms; and further wherein the product obtained is dried under reduced pressure or is dried and optionally maintained under relative humidity conditions greater than or equal to 40%.

3. The process according to claim 2, wherein the water/alcohol or water/ketone final ratio by volume ranges from 3/1 to 1/3.

4. The process according to claim 2, wherein the alcohol is ethanol and the ketone is acetone.

5. The process according to claim 2, wherein the drying or the drying and optional maintaining under a relative humidity greater than or equal to 40% is carried out at a temperature of about 40° C. under a pressure of about 5 kPa and wherein said product contains between 3 and 5% of water.

6. The process according to claim 2, wherein the preparation is carried out directly from an ethanolic solution of 4,10β-diacetoxy-2α-benzoyloxy-5β,20-epoxy-1-hydroxy-9-oxo-19-norcyclopropa(g)tax-11-en-13α-yl (2R,3S)-3-tert-butoxycarbonylamino-2-hydroxy-3-phenylpropionate which is obtained by deprotection, in an acid medium, of the ester 4,10β-diacetoxy-2α-benzoyloxy-5β,20-epoxy-1-hydroxy-9-oxo-19-norcyclopropa(g)tax-11-en-13α-yl (2R,4S,5R)-3-tert-butoxycarbonyl-2-(4-methoxyphenyl)-4-phenyloxazolidine-5-carboxylate.

* * * * *